(12) United States Patent
James et al.

(10) Patent No.: US 8,430,913 B2
(45) Date of Patent: Apr. 30, 2013

(54) DEVICES AND METHODS FOR ADDING AN ADDITIONAL LEVEL OF FIXATION TO AN EXISTING CONSTRUCT

(75) Inventors: Anthony James, Shelton, CT (US); Timothy E. Adamson, Charlotte, NC (US); Scott McLean, Waterbury, CT (US)

(73) Assignee: Spine Wave, Inc., Shelton, CT (US)

( * ) Notice: Subject to any disclaimer, the term of this patent is extended or adjusted under 35 U.S.C. 154(b) by 299 days.

(21) Appl. No.: 12/797,682

(22) Filed: Jun. 10, 2010

(65) Prior Publication Data
US 2010/0318131 A1    Dec. 16, 2010

Related U.S. Application Data

(60) Provisional application No. 61/185,718, filed on Jun. 10, 2009.

(51) Int. Cl.
*A61B 17/70* (2006.01)
*A61B 17/88* (2006.01)

(52) U.S. Cl.
USPC ............ 606/264; 606/279; 606/265; 606/272

(58) Field of Classification Search .................. 606/264, 606/265, 258, 257
See application file for complete search history.

(56) References Cited

U.S. PATENT DOCUMENTS

| | | | |
|---|---|---|---|
| 5,334,203 A | 8/1994 | Wagner | |
| 5,569,246 A | 10/1996 | Ojima et al. | |
| 5,984,923 A | 11/1999 | Breard | |
| 6,077,262 A * | 6/2000 | Schlapfer et al. | 606/305 |
| 6,187,005 B1 | 2/2001 | Brace et al. | |
| 6,273,914 B1 | 8/2001 | Papas | |
| 6,379,354 B1 | 4/2002 | Rogozinski | |
| 6,488,682 B2 | 12/2002 | Kikuchi et al. | |
| 6,626,904 B1 | 9/2003 | Jammet et al. | |
| 6,802,844 B2 | 10/2004 | Ferree | |
| 7,207,992 B2 | 4/2007 | Ritland | |
| 7,645,294 B2 | 1/2010 | Kalfas et al. | |
| 7,695,499 B2 | 4/2010 | Morrison et al. | |
| 8,021,399 B2 | 9/2011 | Ritland | |
| 2002/0143328 A1* | 10/2002 | Shluzas et al. | 606/61 |
| 2005/0277923 A1* | 12/2005 | Sweeney | 606/61 |
| 2006/0036242 A1* | 2/2006 | Nilsson et al. | 606/61 |
| 2006/0142758 A1 | 6/2006 | Petit | |
| 2006/0149244 A1* | 7/2006 | Amrein et al. | 606/61 |

(Continued)

FOREIGN PATENT DOCUMENTS
DE 9402695 5/1994

*Primary Examiner* — Eduardo C Robert
*Assistant Examiner* — James Palmer
(74) *Attorney, Agent, or Firm* — Hoffmann & Baron, LLP

(57) ABSTRACT

A method and assembly is provided for linking an additional vertebral construct to an existing spinal construct having at least two bone screws engaged to corresponding vertebrae and connected by a connecting member. The assembly includes a fastener configured to engage a bone screw of the existing construct and to engage a connecting member connected to the bone screw. The assembly further includes a linking member having an elongated portion configured to connect to a bone screw of the additional construct and a mounting structure configured for mounting on the bone screw of the existing construct. A locking member fixes the orientation of the linking member relative to the bone screw and a clamping member locks the linking member and existing connecting member to the bone screw of the existing construct.

8 Claims, 7 Drawing Sheets

U.S. PATENT DOCUMENTS

| | | |
|---|---|---|
| 2006/0276794 A1 | 12/2006 | Stern |
| 2007/0198014 A1* | 8/2007 | Graf et al. .................... 606/61 |
| 2007/0233091 A1 | 10/2007 | Naifeh et al. |
| 2007/0250061 A1 | 10/2007 | Chin et al. |
| 2008/0183215 A1 | 7/2008 | Altarac et al. |
| 2009/0177232 A1 | 7/2009 | Keiester |
| 2010/0256683 A1 | 10/2010 | Iott et al. |

* cited by examiner

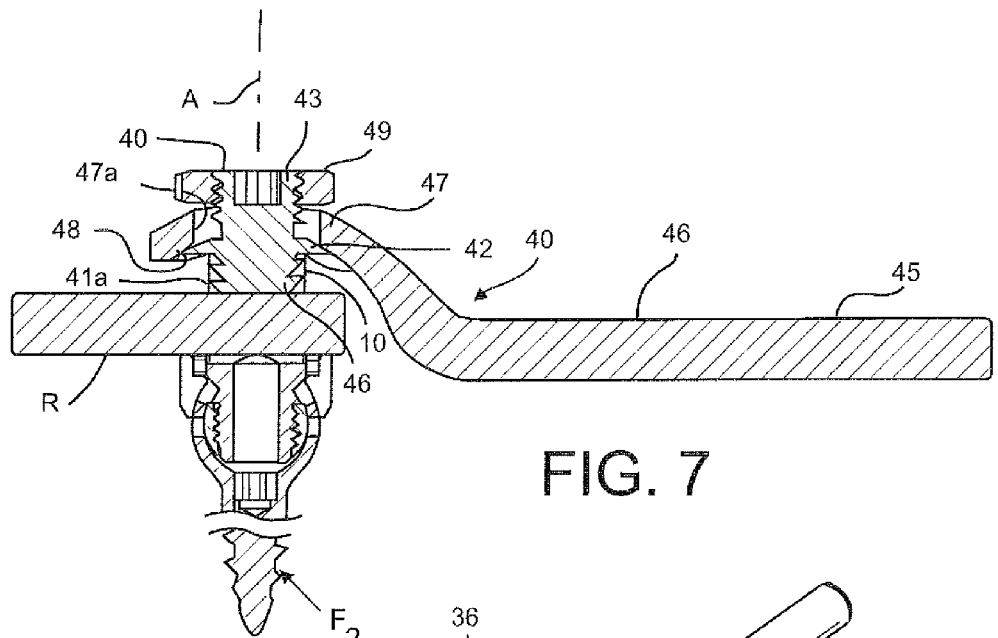
FIG. 7
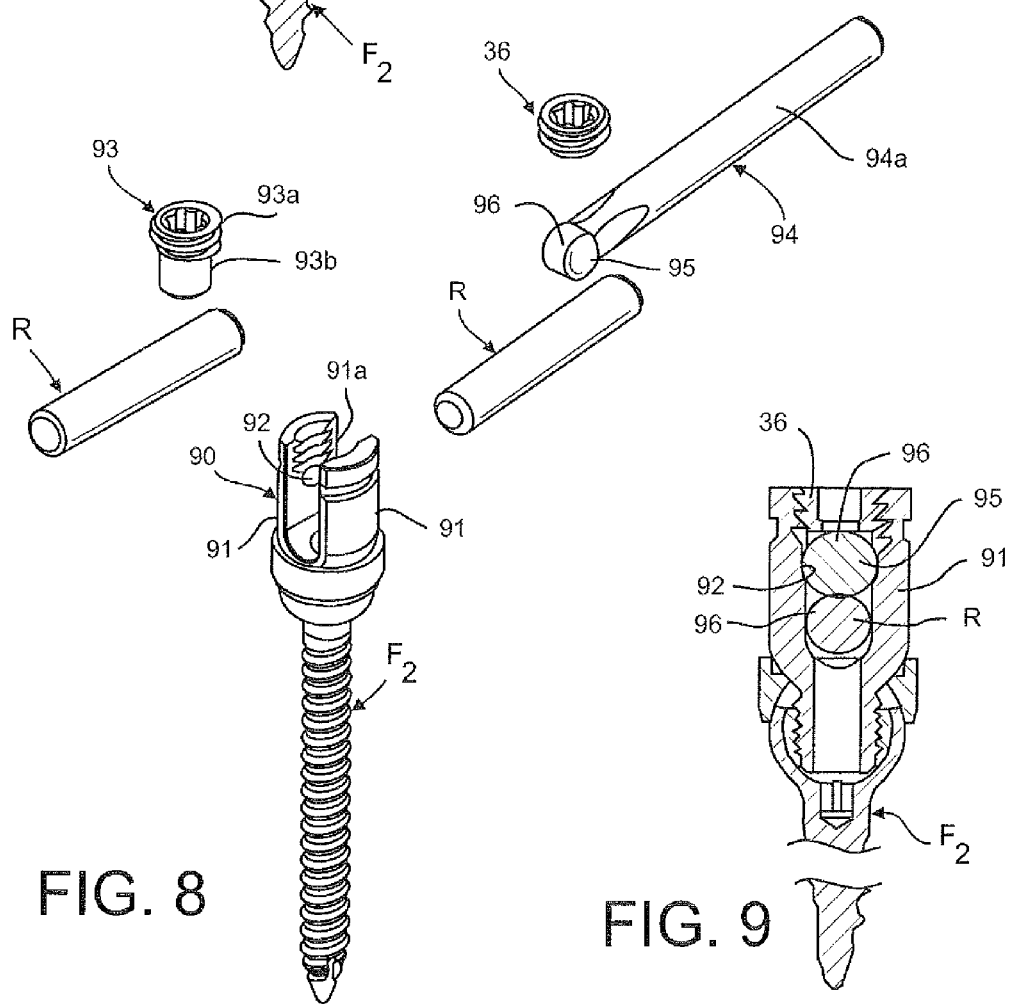
FIG. 8
FIG. 9

DEVICES AND METHODS FOR ADDING AN ADDITIONAL LEVEL OF FIXATION TO AN EXISTING CONSTRUCT

CROSS REFERENCE TO RELATED APPLICATION

The present application claims priority to co-pending provisional application No. 61/185,718, filed on Jun. 10, 2009, the disclosure of which is incorporated in its entirety herein by reference.

BACKGROUND

An emerging trend in spinal fixation is an increased incidence of adjacent disc degeneration subsequent to a previous fixation or fusion. This subsequent degeneration often requires fixation or fusion of additional levels of the spine. Current techniques require exposure of the entire prior construct to access all of the existing bone fasteners to permit removal of the connecting member spanning the fasteners. The connecting member is removed and replaced with a longer member, such as a rod, to engage an additional bone fastener added at the new levels to be instrumented.

This required exposure of the prior fixation construct complicates and lengthens the surgical procedure for adding the additional level of fixation. The current technique is particularly problematic for a fixation construct spanning three or more vertebral levels. There is a need for a device and method that facilitates the addition of further levels of fixation.

SUMMARY

A method is provided for linking an additional vertebral construct to an existing spinal construct having at least two bone engaging fasteners engaged to corresponding vertebrae and connected by a connecting member, the additional vertebral construct including an additional bone engaging fastener engaged to an additional vertebra, in which the bone engaging fasteners include a fastener for locking a connecting member thereto. The method may comprise removing the fastener from one bone engaging fastener of the existing construct, mounting a linking element on the one bone engaging fastener with the connecting element of the existing spinal construct connected to the one bone engaging fastener; clamping the linking element to the yoke of the one bone engaging fastener; and clamping the linking element to the additional bone engaging fastener.

In another aspect, an assembly is provided for linking an additional vertebral construct to an existing spinal construct having at least two bone engaging fasteners engaged to corresponding vertebrae and connected by a connecting member, the additional vertebral construct including an additional bone engaging fastener engaged to an additional vertebra, in which the bone engaging fasteners are configured to receive a connecting member and include a fastener for clamping the connecting member to the bone engaging fastener. The assembly may comprise a linking member including an elongated portion configured similar to the connecting member and sized to span from a bone engaging fastener of the existing construct to the additional bone engaging fastener, and a mounting structure attached to the elongated portion and configured for mounting on the bone engaging fastener of the existing construct. A clamping member is configured to clamp the linking member to the bone engaging fastener of the existing construct with the connecting member connected to the same bone engaging fastener.

DESCRIPTION OF THE FIGURES

FIG. 7 is a side cross-sectional view of the linking element attached to tithe bone engaging fastener shown in FIG. 8.

FIG. 8 is an exploded view of a bone engaging fastener with a modified yoke with alternative rod and rod-linking element features.

FIG. 9 is an end cross-sectional view of a rod-linking element feature attached to a bone engaging fastener shown in FIG. 8.

DESCRIPTION OF THE EMBODIMENTS

Figure 1:
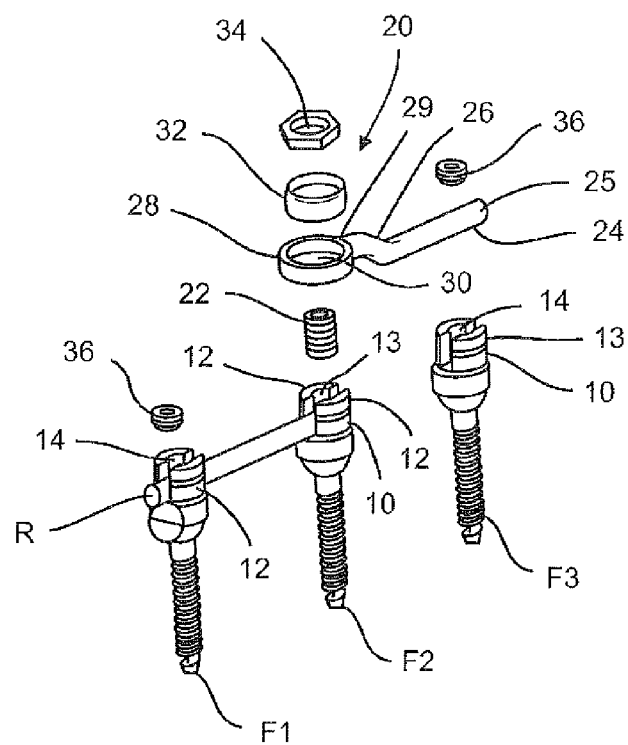
FIG. 1 is an exploded view of a spinal fixation construct with a linking element for adding an additional level of fixation.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
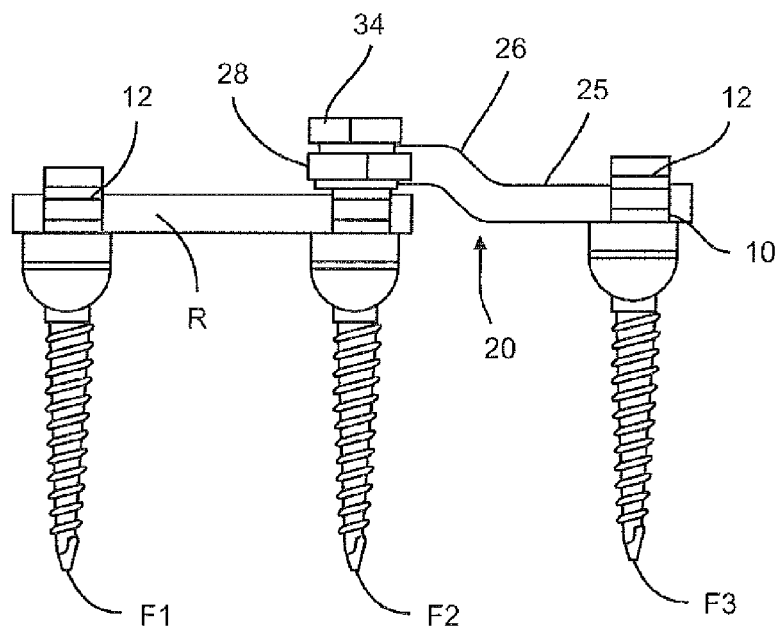
FIG. 2 is a side view of an assembled spinal fixation construct including the linking element shown in FIG. 1.

Referring to FIGS. 1 and 2, an existing construct is shown that includes a pair of bone-engaging fasteners $F_1$ and $F_2$, and an elongated connecting member R. The fasteners may be pedicle screws and the connecting member a rod as illustrated in the figures, although other forms of these components are contemplated. The fasteners $F_1$ and $F_2$ may be hooks or monoaxial bone screws, but for the present disclosure the fasteners are multi-axial screws configured to be engaged within the pedicles of adjacent vertebrae. Further details of such a multi-axial bone screw are described in co-pending application Ser. No. 11/560,587, filed on Nov. 16, 2006, and published as No. 2008/0119857, which is assigned to the assignee of the present application, the disclosure of which is incorporated herein by reference.

In general terms, the bone screws include a yoke 10 with opposite branches 12 forming a slot 13 for receiving the connecting rod R. The opposite branches include internal threads 14 for receiving a fastener, such as set screw 36, that is tightened to lock the connecting member R to the fastener $F_1$ in a known manner. It can be appreciated that these components of the existing construct are appropriately engaged to the vertebral bodies at the instrumented spinal levels. The construct may extend along multiple spinal levels, include more than two bone screws $F_1$ and $F_2$ and incorporate a longer spinal rod R than is depicted in FIG. 1.

Figure 3:
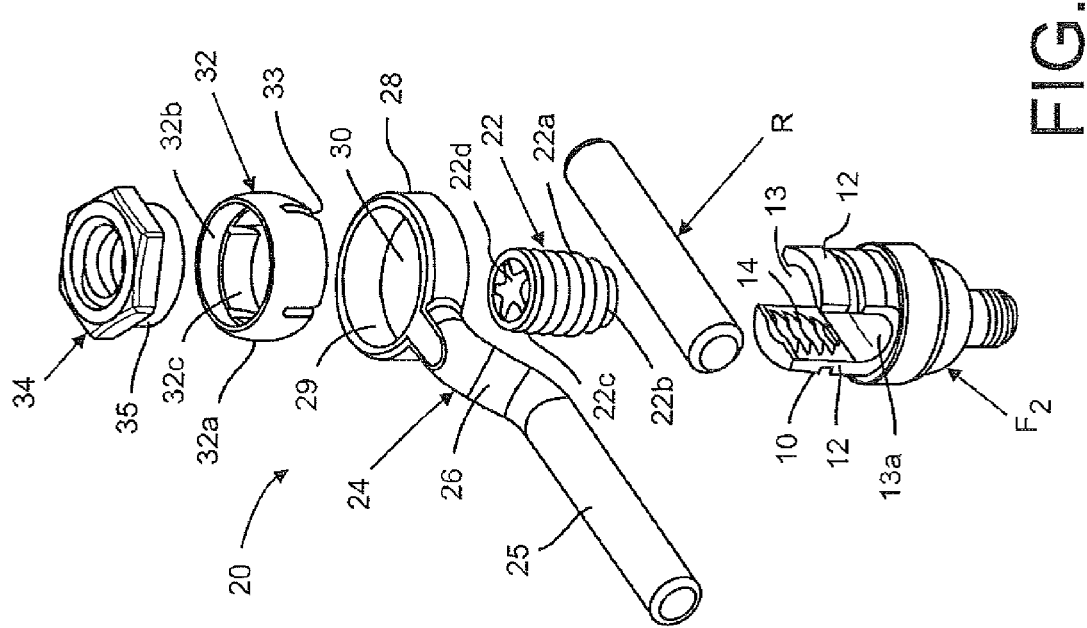
FIG. 3 is an exploded detail view of the linking assembly and one of the bone engaging fasteners shown in FIGS. 1 and 2.
Figure 4:
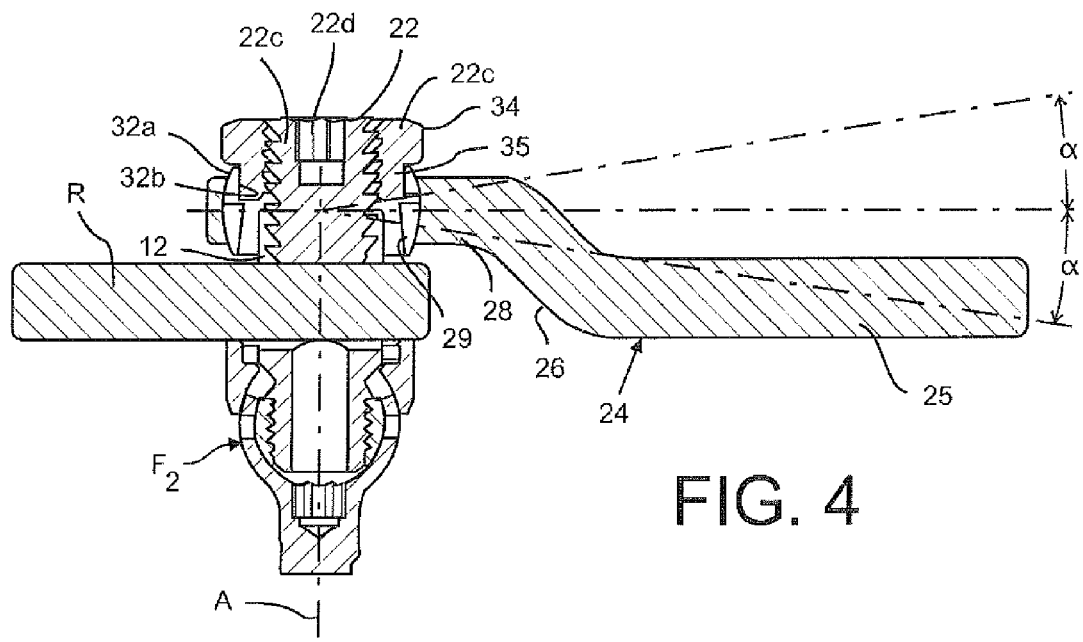
FIG. 4 is a side cross-sectional view of the linking assembly engaged to one of the bone engaging fasteners shown in FIG. 2.
Figure 5:
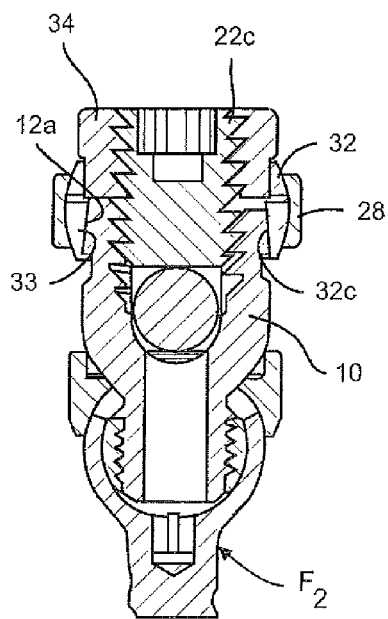
FIG. 5 is an end cross-sectional view of the linking assembly engaged to one of the bone engaging fasteners shown in FIG. 2.

A linking assembly 20 is provided that permits extension of the $F_1$-$F_2$ construct to an additional vertebral level, or more particularly to link to an additional bone screw $F_3$. As best seen in FIGS. 3-5, the assembly 20 includes a linking member 24 that is configured to extend the fixation construct to the additional bone screw $F_3$. Thus, the linking member 24 includes an elongated bar 25 that may emulate the connecting member R. In other words, where the connecting member is a spinal rod, the bar 25 is configured as a rod. Where the connecting member is a spinal plate, the bar 25 is also configured as a plate.

The linking member 24 further includes a mounting structure connected to the elongated bar that is configured to mount the linking member to the existing fixation construct, or more particularly to the yoke of a bone engaging fastener of the construct. In one embodiment, the mounting structure includes a collar 28 that has an inner surface 29 defining an opening 30 therethrough. In one embodiment, the opening 30 is sized so that the collar can be received over the branches 12 of the yoke 10 of one of the bone-engaging fasteners $F_2$, thereby permitting the linking member to rotate about the longitudinal axis A of the fastener $F_2$. In certain embodiments, the collar 28 may bear directly on the connecting rod R disposed within the yoke 10, which limits the ability of the linking element 24 to pivot about an axis transverse to the longitudinal axis A of the fastener $F_2$. However, in other embodiments the collar 28 is supported above the rod R, as described below, so that the linking element may pivot through the angle ±α shown in FIG. 4.

The linking assembly 20 further includes a fastener that is configured to engage the yoke to clamp the rod within the yoke. In one embodiment, the fastener is an extended set screw 22 that has a lower threaded portion 22a that is configured to engage the internal threads 14 of the yoke 10. The lower portion 22a of the set screw defines a tip 22b that is configured to engage and restrain the spinal rod R within the yoke. The set screw further includes an upper portion 22c that is configured to engage a clamping member, such as nut 34 as described herein. The upper portion 22c defines a tool recess 22d for engagement by a driving tool, such as a hex or Torx wrench.

In the existing construct, fasteners, such as the set screw 36, are used to fix the rod R within the yoke of each bone screw $F_1$ and $F_2$. These set screws are preferably sized to be completely contained within the confines of the branches 12. In other words, the set screws have a height that is slightly less than the depth of the slot 13 with the rod R therein. However, the extended set screw 22 may be sized to extend beyond the upper end of the yoke 10. Thus, in one embodiment the extended set screw 22 has a height sufficient to pass through the collar 28 and mate with the nut 34, as shown in FIGS. 4 and 5. In a specific embodiment, the extended set screw 22 has a height at least equal to depth of the slot 13 to the rod R therein plus the height of the collar 28. In one embodiment the nut 34 may include an internally threaded sleeve 35 that is configured to engage the set screw 22 within the collar. In another embodiment, the set screw 22 has a height so that the upper portion 22c projects above the collar 28 and engage the nut 34 without the sleeve. In a further embodiment, the upper portion 22c and nut 34 are configured for mutual locking engagement so that the tip 22b of the set screw 22 exerts a clamping pressure on the rod R when the lower portion 22a is threaded into the yoke and the upper portion 22c and nut 34 are engaged with the nut bearing on the collet 32, as described herein.

The linking assembly 20 is shown in FIG. 2 fastened to the existing construct. The bar 25 of the linking element 24 is configured to fit within the yoke 10 of an additional bone-engaging fastener $F_3$ using a conventional set screw 36. The linking element 24 may include a bend 26 that allows the third fastener $F_3$ to be situated at the same prominence as the other fasteners of the existing construct.

In one embodiment, the cavity 29 mates with a locking element 32 disposed within the collar 30. The locking element may be an expandable element, such as a collet. The cavity 29 may be spherical to mate with a generally spherical outer surface 32a of the collet 32 disposed within the opening 30 of the collar 28. The collar 28 and collet 32 are configured to fit over the extended set screw 22 so that the set screw can be engaged by the nut 34. The spherical cavity 29 and spherical collet 32 form an articulating interface that allows the linking element 24 to achieve different angular orientations relative to the existing construct. Thus, in addition to rotating about the longitudinal axis A of the fastener $F_2$, the linking element 24 can pivot upward or downward at an angle ±α relative to the existing fasteners. This pivoting can be in combination with rotation about the axis A. The provision of this articulating interface adds flexibility to the linking assembly 20 to integrate the existing construct with the additional bone fastener.

The linking assembly 20 is engaged to the existing construct by tightening the nut 34 onto the extended set screw 22 so that the nut bears down on the collet 32. The collet 28 may be provided with a generally cylindrical interior portion 32b to receive the generally spherical sleeve 35 of the nut 34. The lower portion 32c of the collet is tapered and includes expandable slits 33 configured to permit expansion of the effective diameter of the collet. The lower portion 32c fits over a similarly tapered portion 12a of the yoke arms 12, as best seen in FIG. 5. As the nut is threaded onto the set screw 22 the head 22c of the nut pressed down on the collet 32, thereby pushing the tapered lower portion 32c against the tapered portion 12a of the yoke arms. This motion thus expands the collet 32 to bear against the collar 28, thereby fixing the additional construct to the existing construct.

It can be appreciated that the set screw 36 that is engaged to the bone screw of an existing construct may be readily replaced by the linking element and associated components shown in FIGS. 3-5. This replacement can occur without disturbing the bone screw $F_2$ or its engagement with the associated vertebra. The rod R of the existing construct may remain situated within the slot 13 of the yoke 10. In instances where compression or distraction is required, the extended set screw 22 may be threaded into the yoke 10 and provisionally tightened onto the rod R. Once the compression or distraction is complete, the extended set screw 22 may be finally tightened onto the rod to complete the original construct. The additional construct may then be added using the linking element 24 as described above.

The collar 28 of the linking element 24 may be modified depending upon the configuration of the yoke 10. For instance, in some bone screws, the branches of the yoke are inwardly deflectable and include upper flanges. The cavity 29 of the collar 28 may be configured for a snap-fit engagement with these branches.

Similarly, the collet 32 may be modified to mate with a particular yoke configuration. In particular, some yoke designs incorporate a tapered upper edge above the internal threads 14. The collet 32 may thus include a lower tapered portion that mates within the tapered upper edge of the yoke 10. The spherical surface of the collet still provides the articulating surface for the spherical cavity 29 of the collar 28.

It can further be appreciated that the linking element 24 may have a length sufficient to extend across multiple vertebral levels and to link with more than one additional fastener $F_3$. The linking element may also be bendable to allow the element to be contoured to engage fasteners at the additional levels.

Figure 6:
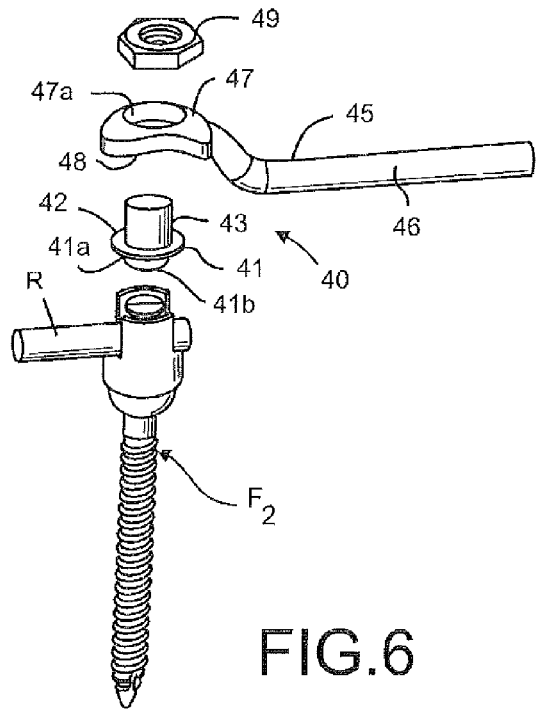
FIG. 6 is an exploded view of a linking element according to a further embodiment for attachment to a bone engaging fastener.

In an alternative embodiment, the set screw 36 of an existing construct, such as the bone screw $F_2$ in FIG. 2, may be replaced by a modified set screw 41 to mate with a linking member 45 of a linking assembly 40, as shown in FIGS. 6 and 7. The set screw 40 includes a lower threaded portion 41a configured to engage the internal threads 14 of the yoke 10 and includes a tip 41b adapted to engage and restrain the spinal rod R within the yoke. The set screw 40 further includes a spherically-shaped flange 42 that is configured to reside above the top of the yoke 10 when the lower threaded portion 41a is fully threaded within the yoke (FIG. 7). The flange 42 is configured to support a mounting structure of the linking member 45. In one embodiment, this mounting structure includes a collar 47. The collar 47 includes a lower spherical surface 48 adapted for articulating contact with the flange 42 so that the linking element 45 may rotate about the axis A and pivot through the angle $\pm\alpha$ as described above. The linking element 45 includes an elongated bar 46 that is used to extend the existing construct in the manner described above. The bar 46 may be similar to the bar 25 in the prior embodiment.

The modified set screw 40 further includes an upper threaded portion 43 that extends through an opening 47a in the collar of the linking element. A jam nut 49 is threaded onto the upper portion 43 to clamp the components together. The jam nut 49 may be provided with a spherical underside to conform to the spherical configuration of the collar 47 of the linking element 45.

In some embodiments, rotation about the longitudinal axis of the bone screw is not necessary. In these embodiments, the linking element and mating components of the above embodiments may be keyed or otherwise configured to prevent such rotation. In an alternative embodiment, a bone screw $F_2'$ may be provided with a modified yoke 90, as illustrated in FIGS. 8-9. In this embodiment, the yoke 90 includes arms 91 that extend upward to a greater height than the arms of the yoke 10 in the prior embodiments. Internal threads 91a are defined at an upper portion of the arms. In a standard construct, the rod R is clamped within the extended yoke by a modified set screw 93. The set screw includes an upper threaded portion 93a configured to engage the internal threads 91a of the yoke. Projecting below the threaded portion is an elongated post 93b adapted to engage and restrain the rod R when the upper threaded portion 93a is fully threaded into the yoke. Thus, the post 93b accounts for the additional height of the yoke arms 91 between the internal threads 91a and the rod R seated within the yoke 90.

An additional level may be added to the construct by removing the modified set screw 93 and introducing a linking element 94, as shown in FIG. 9. The linking element includes a bar 94a that may be configured like the bars described above. The element includes a generally spherical knob 95 at one end that is adapted to seat within dimples 92 formed in the inner surface of the arms 91 of the yoke 90, as shown in FIG. 9. The knob 95 includes a generally cylindrical surface 96 contacting the rod R and the set screw 36 threaded into the upper threaded portion of the yoke. The cylindrical surface thus allows the linking element 94 to pivot through the angle $\pm\alpha$, but the engagement of the knob 95 within the dimples 92 prevents rotation of the element about the axis of the bone screw. It can be appreciated in this embodiment that the set screw used to lock the linking element and components together may be the same as the set screw 36 used in the original construct shown in FIG. 1.

Figure 10:
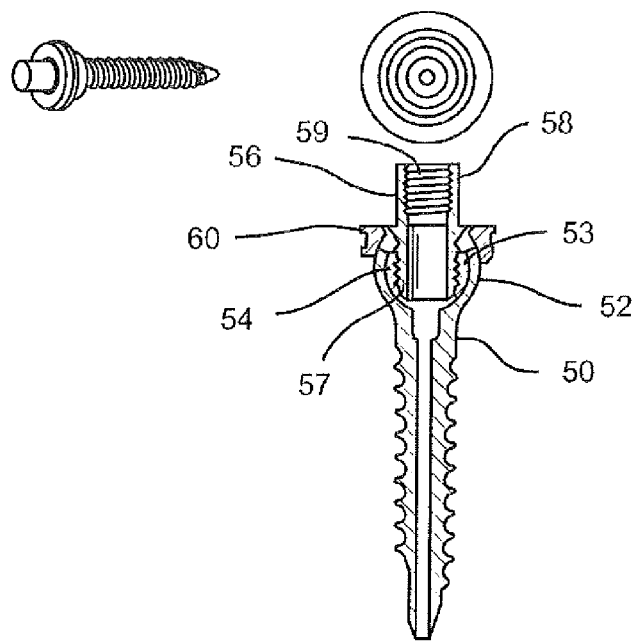
FIG. 10 is a cross-sectional view of a variable angle bone screw.

A modified bone screw 50 is shown in FIG. 10 that includes a head 52 defining an internal spherical cavity 53. A spherical insert 54 is disposed within the cavity and engages a mating stem 56 at a threaded engagement 57. A locking sleeve 60 is provided that is used to lock the articulating components together when the construct is finalized. The bone screw as thus far described is similar to the bone screw disclosed in the published application No. 2008/0119857 incorporated by reference above. In the modified bone screw, the mating stem 56 includes an upper stem portion 58 that is adapted to engage a generally planar connecting element, such as a bone plate. The upper stem portion 58 include threads, such as internal threads 59, to engage a nut or a bolt to clamp the bone plate to the bone screw 50.

An existing bone plate construct may be extended using a linking element 65 as shown in FIGS. 11-15. The linking element 65 includes a support washer 68 that includes a ring 69 defining an opening 70 for receiving the upper stem portion 58 of an existing bone screw therethrough. A mounting hub 72 and an alignment hub 73 are defined on an upper surface of the ring 69. A pair of attachment beams 75 are pivotably mounted to the mounting hub 72 by a hinge pin 76 so that the beams can pivot downward, as shown by the arrow in FIG. 11, and straddle the alignment hub 73.

Figure 11:
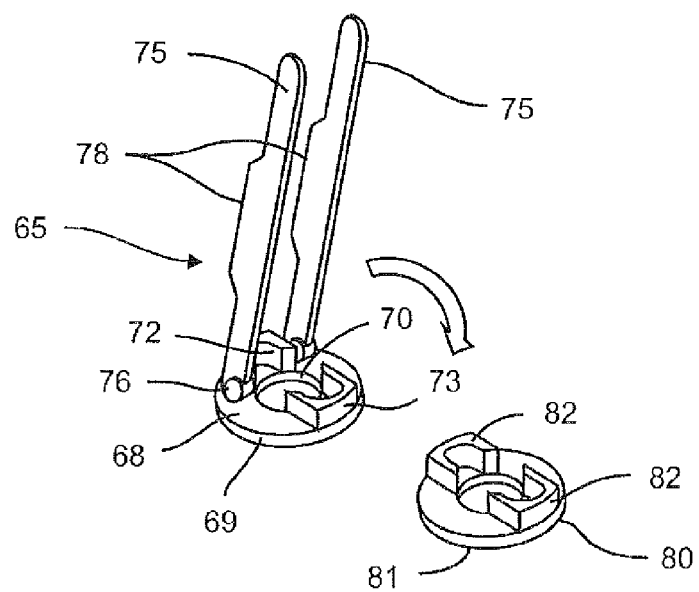
FIG. 11 is a perspective view of a linking element configured for attachment to the bone screw shown in FIG. 10.

The attachment beams 75 are configured to engage an attachment washer 80 supported on an additional bone screw. The attachment washer is configured similar to the washer 68 but without the pivotably mounted beams. Thus, the washer 80 includes a ring 81 with a pair of alignment hubs 82 that are straddled by the attachment beams 75 when they are pivoted forward as shown in FIG. 11.

Figure 15:
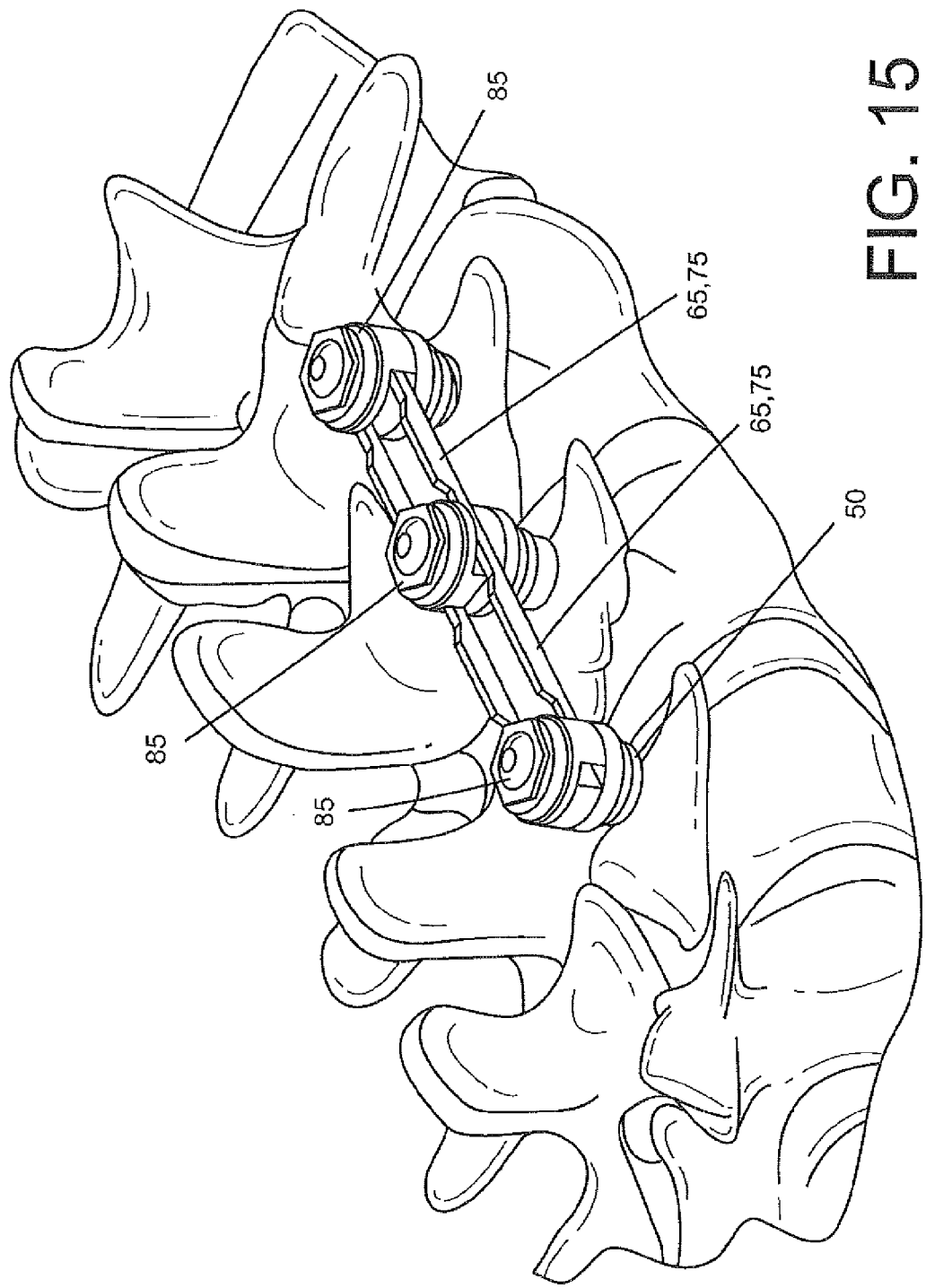
FIG. 15 is a representation of a spinal fixation construct utilizing the bone engaging fastener, linking element and locking cap shown in FIGS. 10-14.

As shown in FIG. 15, the support washer 68 is mounted on the upper stem portion 58 of a bone screw 50 that is engaged within a vertebra. The attachment washer 80 is mounted on the upper stem portion of the next successive bone screw. Both washers are seated on the locking sleeve 60 (FIG. 10) of the bone screw 50. The attachment beams 75 are then pivoted forward onto the attachment washer.

Figure 13:
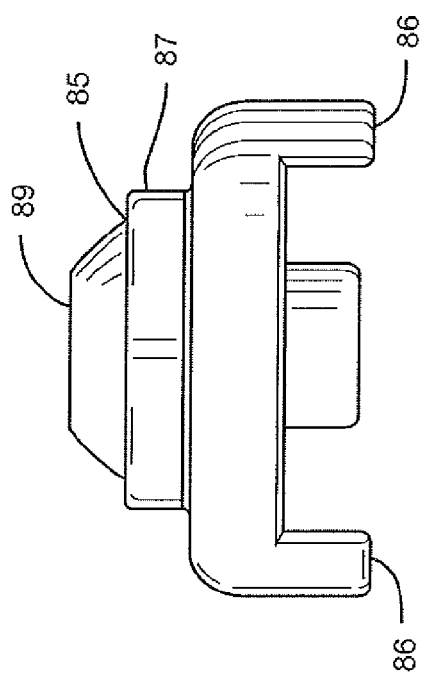
FIGS. 12-14 are perspective, side and bottom views of a locking cap for locking the linking element of FIG. 11 to the bone screw of FIG. 10.
Figure 14:
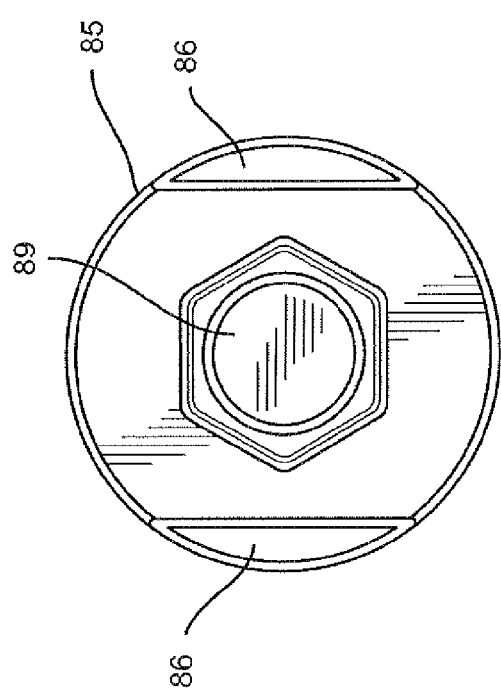
Figure 12:
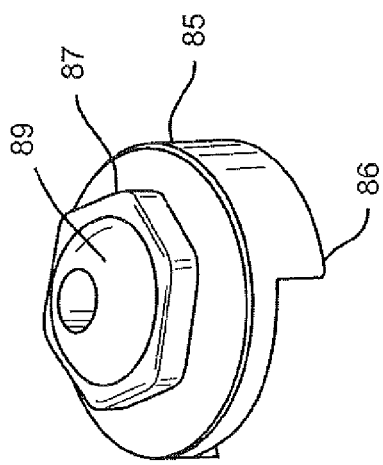

The beams may be fixed in place by the cap 85 shown in FIGS. 12-14. The cap 85 includes alignment arms 86 that are complementary with the hubs 72, 73 on the support washer 68 and the hubs 82 on the attachment washer 80. The arms 86 bear against the sides of the attachment beams 75 to trap the beams between the arms of the cap 80 and the hubs. The cap includes a set screw 89 extending through a central boss 87 in alignment with the internal threads 59 of the upper stem portion 58 of the bone screw. Tightening the set screw 89 into the threads of the upper stem portion not only fixes the attachment beams 75 to the respective washers, but also tightens the bone screw construct as the spherical insert 54 engages the cavity 53, the washers 68, 80 are pressed into the locking sleeve 60 and locking sleeve is pressed into the head 52 of the bone screw.

The hubs 72, 73 of the support washer 68 and hubs 82 of the attachment washer 80 may define an internal configuration that is adapted to receive an insertion tool. The internal configuration may be, for instance, an undercut that can be engaged by a forceps-type tool to hold the washer and guide it into position over the upper stem portion 58 of a bone screw. The cap 85 may incorporate an internal hex at the underside of the cap to engage a similarly configured section of the upper stem portion 56 of the bone screw. The boss 87 may also have a hex configuration to engage a torque wrench.

The attachment beams 75 may include a raised center portion 78 to offset the moment of inertia of the beams. The beams may also be beveled at their leading edges to facilitate passage of the beams through tissue adjacent the implant site.

The linking elements disclosed herein may be engaged to bone fasteners of an existing construct in situ. The linking elements provide structure for linking an additional bone fastener or fasteners to the existing construct by removing only one locking element at the end of the construct. The connecting element of the existing construct remains undisturbed as the linking elements are added.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An assembly for linking to an existing spinal construct, said existing spinal construct having at least two bone engaging fasteners engaged to corresponding vertebrate and connected by a connecting member in which the bone engaging fasteners each include a yoke receiving said connecting member seated therein and a fastener clamping the connecting member within the yoke of at least one of said bone engaging fasteners, said assembly comprising:
    an elongate fastener having an upper portion and a lower portion, said lower portion being configured to engage the yoke of another of said bone engaging fasteners and comprising a tip at said lower portion configured to engage said connecting member seated within the yoke of said another bone engaging fastener when said tip is in engagement with said connecting member;
    a linking member having an elongated portion and a mounting structure, said mounting structure being configured for mounting on the yoke of said another of said bone engaging fasteners and including a collar defining an opening therethrough for receipt therethrough of said upper portion of said elongate fastener;
    a locking member disposed within said opening in said collar; and
    a clamping member configured to threadably engage the upper threaded portion of said elongate fastener when extending through the opening in said collar and further configured to lock said locking member to said collar when engaged to said elongate fastener.

2. The assembly according to claim 1, wherein:
    said locking member includes an expandable collet disposed within said opening of said collar, said collet defining a collet opening; and
    said clamping member includes a nut threaded to engage said upper portion of said fastener and configured to bear against said collet as said nut is threaded onto said upper portion.

3. The assembly according to claim 2, wherein:
    said collar defines a spherical surface at said opening; and
    said collet includes a generally spherical outer surface for articulating contact with said spherical surface of said collar.

4. The assembly according to claim 2, in which the yoke of said another of said bone engaging fasteners includes a tapered outer surface, wherein said collet includes a tapered inner surface configured for mating contact with the tapered outer surface of the yoke.

5. The assembly according to claim 1, wherein said linking member includes a bend between said collar and said elongated portion.

6. The assembly according to claim 1, further including an additional bone engaging fastener for engaging an additional vertebra, wherein said additional fastener comprises a multi-axial pedicle screw.

7. An assembly for linking to an existing spinal construct, said existing spinal construct having at least two bone engaging fasteners engaged to corresponding vertebrae and connected by a connecting member in which the bone engaging fasteners each include a yoke receiving said connecting member seated therein and a fastener clamping the connecting member within the yoke of at least one of said bone engaging fasteners, said assembly comprising:
    an elongate fastener comprising an upper portion, a lower portion and a flange between said upper and lower portions, said flange defining a generally spherical upper surface, said lower portion being configured to engage the yoke of another of said bone engaging fasteners and comprising a tip at said lower portion configured to engage said connecting member seated within the yoke of said another bone engaging fastener;
    a linking member having an elongated portion and a mounting structure configured for mounting the linking member on the yoke of said another of said bone engaging fasteners, said mounting structure including a generally spherical lower surface configured for articulating contact with said upper surface of said flange; and
    a clamping member configured to engage said upper portion of said elongate fastener to clamp said mounting structure of said linking member between said clamping member and said flange of said fastener.

8. The assembly according to claim 7, wherein said linking member includes a bend between said collar and said elongated portion.

* * * * *